US006841524B1

(12) United States Patent
Patel et al.

(10) Patent No.: US 6,841,524 B1
(45) Date of Patent: Jan. 11, 2005

(54) LOW SURFACTANT, HIGH SUGAR BARS

(75) Inventors: Rajesh Patel, Lyndhurst, NJ (US); Joseph Oreste Carnali, Pompton Plains, NJ (US); Ritu Verma, New York, NY (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/682,698

(22) Filed: Oct. 9, 2003

(51) Int. Cl.[7] .................................................. A61K 7/50

(52) U.S. Cl. ....................... 510/151; 510/152; 510/470; 510/481

(58) Field of Search ................................ 510/141, 151, 510/152, 470, 481

(56) References Cited

U.S. PATENT DOCUMENTS

| | | | | | |
|---|---|---|---|---|---|
| 5,194,172 | A | * | 3/1993 | Taneri et al. | 510/145 |
| 5,910,476 | A | * | 6/1999 | Kinsman et al. | 540/447 |
| 5,919,744 | A | * | 7/1999 | Lazarowitz | 510/147 |
| 6,046,147 | A | * | 4/2000 | Cassady et al. | 510/153 |
| 6,174,845 | B1 | | 1/2001 | Rattinger et al. | |
| 6,224,812 | B1 | | 5/2001 | Allan et al. | |
| 6,376,441 | B1 | | 4/2002 | Ross et al. | |
| 6,383,999 | B1 | | 5/2002 | Coyle et al. | |
| 6,384,000 | B1 | | 5/2002 | McFann et al. | |
| 6,458,751 | B1 | | 10/2002 | Abbas et al. | |
| 6,462,002 | B2 | | 10/2002 | Saxena et al. | |

FOREIGN PATENT DOCUMENTS

| | | | |
|---|---|---|---|
| WO | 01/58422 | A2 | 8/2001 |
| WO | 02/50226 | A1 | 6/2002 |
| WO | 02/061030 | A2 | 8/2002 |

* cited by examiner

*Primary Examiner*—Necholus Ogden
(74) *Attorney, Agent, or Firm*—Ronald A. Koatz

(57) ABSTRACT

The present composition comprises bar having small amounts of surfactant and high amounts of sugars which bar maintains good rates of wear and foams adequately. The sugar has unexpectedly been found to structure bars, even when little or no insoluble fatty acid is used, without degrading bar properties.

9 Claims, No Drawings

LOW SURFACTANT, HIGH SUGAR BARS

FIELD OF THE INVENTION

The invention relates to bar compositions (e.g., beauty or toilet bar compositions), preferably soap bar compositions, comprising relatively low levels of surfactant and high levels of sugars.

BACKGROUND OF THE INVENTION

Traditionally, soap bars are composed of mixtures of soluble fatty acid soaps (which deliver lather benefits) and insoluble fatty acid soaps (which confer bar structure). For a variety of reasons, it may be desirable to reduce the levels of soluble and insoluble surfactant components in bar compositions, whether their components be soluble and insoluble fatty acid soaps or soluble and insoluble synthetic surfactant. High levels of surfactant, particularly if the surfactant is fatty acid soap for example, may decrease mildness.

A reduction in surfactant level, however, may have other consequences. For example, reduction in insoluble surfactant (e.g., insoluble fatty acids) must be accompanied by an increase in the level of fillers or other ingredients which in turn may lead to higher rates of wear. Also, for example, it would be expected that a reduced level of soluble surfactant would decrease foam generation, whereas foam is a desirable consumer cue of good cleansing.

As noted, it might be expected that reducing the level of surfactant (e.g., to increase mildness) and replacing the surfactant instead with fillers would lead to high rates of bar wear and poor foam properties (see, for example, U.S. Pat. No. 6,462,002 to Saxena et al.).

Unexpectedly, however, applicants have found that it is possible to avoid or minimize the use of insoluble fatty acids (which enhance structure but inhibit foam) by using bars which have relatively high levels (e.g., greater than about 40%) of sugar. The high levels of sugar have been found to confer structure even with little or no insoluble fatty acid, while avoiding the foam depressing effects of insoluble fatty acids. Further, because of the overall low surfactant levels, the bars provide enhanced mildness. Further, the sugars (e.g., sucrose and disaccharides) are inexpensive and can easily be incorporated into soap bars.

Bars disclosed in the art typically may have relatively high levels of surfactants and relatively low levels of hydrophilic emollients. WO 02/50226 (Unilever), for example, discloses a low water cleansing bar comprising 15% to 60% by wt. surfactant and hydrophilic emollient (which may include polyhydric alcohols such as glycerine and propylene glycol, and polyols such as polyethylene glycols) at levels of 5 to 20%.

Similarly, U.S. Pat. No. 6,376,441 B1 to Ross et al. discloses multi-phase melt cast bars wherein, according to the examples, soap is present at about 40% by wt. and the level of sugar is about 16.8% (delivered as a 70% sucrose solution in water).

Other documents of interest may include the following: U.S. Pat. No. 6,458,751 to Abbas et al.; U.S. Pat. No. 6,384,000 to McFann et al.; U.S. Pat. No. 6,383,999 to Coyle et al.; U.S. Pat. No. 6,224,812 to Allan et al.; U.S. Pat. No. 6,174,845 to Rattinger et al.; WO 2002/061030 to Abbas et al., and WO 01/58422 to Coyle et al.

In none of the art is there believed disclosed bars having relatively low levels (e.g., less than about 25% by wt.) of surfactants comprising soluble fatty acid soaps and detergents and little (less than 5%, preferably less than 3%, more preferably less than 2% and most preferably less than 1%) or no insoluble fatty acid soaps; all in combination with high levels (greater than about 40%, preferably greater than about 50%) of sugars.

BRIEF SUMMARY OF THE INVENTION

The present invention comprises bar compositions, preferably surfactant bar compositions, more preferably fatty acid soap and optionally synthetic detergent compositions comprising:

(1) less than about 25%, preferably less than about 20% by wt. surfactant (including soluble fatty acids soaps and detergents and less than about 5% insoluble fatty acid soap);

(2) greater than about 40%, preferably greater than about 50% to about 80% by wt., preferably to about 70% by wt. sugar or combination of sugars;

(3) about 5% to 25% by wt of a glass transition temperature modifier; and (4) about 1% to about 30%, preferably 5–30% water.

DETAILED DESCRIPTION OF INVENTION

The present invention relates to bar compositions having less than about 25% surfactant, more than about 40% sugar and about 5% to 25% glass transition temperature modifier. Moreover, the surfactant comprises predominantly soluble fatty acid soap and detergent and the amount of insoluble fatty acid soap is less than about 5% of the bar composition.

Previously, it has not been considered to prepare relatively low surfactant, high sugar bars because the removal of insoluble fatty acid soaps (and replacement with filler) would have been believed to lead to high wear or mush rate (caused by the increased fillers replacing insoluble fatty acid soap or synthetic) and/or to reduced foam levels (caused by reduced soluble fatty acid soaps which soluble soaps help foaming).

For purpose of the invention, soluble fatty acid soaps are defined as soaps soluble in water to at least 2% at 35° C.; and insoluble soaps are those failing this criteria.

More specifically, the bar compositions of the invention comprise:

(1) less than 25% by wt. of total composition, preferably less than 20% by wt. total composition of surfactant (preferably the surfactant is or comprises predominantly, e.g., greater than 75%, preferably greater than 90% of total surfactant, soluble fatty acid soap; also, less than 5%, preferably less than 3%, more preferably less than 2%, most preferably less than 1% of compositions comprises insoluble fatty acid);

(2) greater than about 40%, preferably greater than 50%, more preferably greater than 55% by wt. sugar or sugars;

(3) about 5% to 25%, preferably 5% to 20% by wt. of a glass transition temperature modifier; and (4) about 1% to 30% water.

The bar compositions of the invention are unique in that they comprise low total surfactant (less than 25%, including little or no insoluble fatty acid), and high sugars, and yet maintain good foaming (e.g., sugar does not depress foam) and low mush (e.g., sugar "fillers" used in place of insoluble surfactant provide structure and do not enhance mush).

The principal surfactant of the subject invention (which surfactant comprises less than about 25% of bar composition) is soap, technically referred to as salts of $C_8$ to $C_{22}$ fatty acid. These fatty acids may be natural or synthetic aliphatic (alkanoic or alkenoic) acid salts. Soaps having the fatty acid distribution of coconut oil may provide the lower end of the broad molecular weight range and are generally referred to as "soluble" fatty acid soaps, as defined above. Those soaps having the fatty acid distribution of peanut, tallow or rapeseed oil, or their hydrogenated derivatives (e.g. $C_{16}$ and higher), may provide the upper end of the molecular weight range and are generally referenced to as insoluble fatty acid soap.

In general soap making, it is preferred to use soaps having the fatty acid distribution of coconut oil or tallow, or mixtures thereof, since these are among the more readily available fats. The proportion of fatty acids having at least 12 carbon atoms in coconut oil soap is about 85%. The proportion will be greater when mixtures of coconut oil and fats such as tallow, palm oil, or non-tropical nut oils or fats are used, wherein the principal chain lengths are $C_{16}$ and higher. For the purposes of this invention, in which the levels of insoluble fatty acid are low or even zero, it is preferred to use primarily coconut oil soaps and mixtures of coconut oil soap and synthetic detergents. Specifically, insoluble fatty acid soaps comprise less than 5%, preferably less than 3%, more preferably less than 2% and more preferably less than 1% of bar composition.

The soaps may contain unsaturation in accordance with commercially acceptable standards. Excessive unsaturation is normally avoided.

Salt counterions to the fatty acid may be those selected from alkali, ammonium or alkanolammonium ions. The term alkanolammonium refers to one, two or three $C_1$–$C_4$ hydroxyalkyl groups substituted onto a nitrogen cation, the triethanolammonium cation being the species of choice. Suitable alkali metal cations are those of potassium and sodium, the latter being preferred.

As indicated, the level of total surfactant should be less than about 25% by wt., preferably less than 20% by wt. of total bar composition. The soap itself (e.g., $C_8$ to $C_{22}$ fatty acid salt but preferably $C_8$ to $C_{12}$ fatty acid salt) comprises greater than 75%, preferably greater than 90% of the surfactant system with the remainder from a synthetic surfactant or detergent.

In this regard, the bar may tolerate small levels of surfactant other than soap (i.e. synthetic detergent) although as noted, total surfactant (including soap) is less than about 25% by wt. of bar composition.

The surfactant may include surfactants selected from the group consisting of anionic surfactants, cationic surfactants, amphoteric surfactants, nonionic surfactants and mixtures thereof.

Anionic Surfactants

Anionic surfactants include, but are certainly not limited to aliphatic sulphate, aliphatic sulfonate (e.g., $C_8$ to $C_{22}$ sulfonate or disulfonate), aromatic sulfonate (e.g., alkyl benzene sulfonate), alkyl sulfoccinates, alkyl and acyl taurates, alkyl and acyl sarcosinates, sulfoacetates, alkyl phosphates, carboxylates, isethionates, etc.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

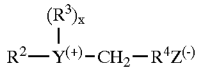

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

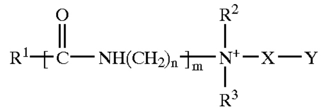

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $—CO_2—$ or $—SO_3—$

Nonionic Surfactants

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Sugars

The commonly occurring crystallizable sugars belong to the class of mono- and disaccharides (Food Theory and Applications, edited by Pauline C. Paul and Helen H. Palmer, Wiley, New York, 1972, ISBN 0-471-67250-5). The class of monosaccharides includes dextrose, fructose, and galactose. The class of disaccharides includes sucrose, the most commonly used sweetener in the confectionery industry and the ingredient usually implied when the term "sugar" is used. Sucrose is a disaccharide composed of glucose and fructose residues joined by an $\alpha,\beta$-glycosidic bond. Other common disaccharides include lactose, maltose, palatinose, and leucrose.

Glass Transition Temperature Modifiers

Non-crystalline or rock candies are formed when supersaturated sugar solutions are cooled to below their glass transition temperature (Tg), at which point a glassy phase forms. The glass transition temperature of a given mono or disaccharide solution depends on the mono- or disaccharide itself, its concentration in water, and the presence of glass transition modifiers (H. Levine and L. Slade, "Cryostabilization Technology: Thermoanalytical Evaluation of Food Ingredients and Systems", in *Thermal Analysis of Foods*, edited by V. R. Harwalkar and C. Y. Ma, Elsevier, 1990, pp 221–305). Without wishing to be bound by theory, it is believed that the role of glass transition temperature modifiers in the present invention is to raise the glass transition temperature of the sugars component of the bar and so increase the bar hardness. For the purpose of this invention, glass transition modifiers are chosen from three distinct classes of compounds, corn sweeteners, water soluble vinyl polymers, and modified, water soluble, celluloses and starches.

Corn Sweeteners

Corn sweeteners are a class of sweeteners derived from corn by hydrolyzing corn starch polymers down into polydextrose units of various lengths. The degree of conversion of the starch molecule is measured by the dextrose equivalent, D. E., which refers to the percent of reducing sugars calculated as dextrose on a dry weight basis. Higher D.E. corn sweeteners are more highly converted and have lower molecular weights. Depending on the degree of conversion of the starch molecule, corn sweeteners are classified as follows:

very low conversion: 20 D.E. and lower;

low conversion: 20–38 D.E.;

regular conversion: 38–48 D.E.;

intermediate conversion: 48–58 D.E.;

high conversion: 58–68 D.E.;

extra high conversion: 68 D.E. and higher.

The degree of conversion affects the functionality of the corn sweetener, lower DE corn sweeteners have a greater effect on increasing the glass transition temperature of their mixtures with sugars. An important class of corn sweeteners in this regard are the maltodextrins, hydrolyzed from starch to a D.E. of less than 20. A comprehensive series of maltodextrins are manufactured by the Grain Processing Corporation under the tradename Maltrin.

Another example is Karo syrup which is a low conversion corn sweetener having a DE of about 32.

Water Soluble Vinyl Polymers

Various water soluble vinyl polymers can be useful as glass transition modifiers as discussed in the Levine and Slade reference noted above. A copy of the reference is hereby incorporated by reference into the subject application. These include poly vinyl pyrrolidone (PVP) and poly ethylene glycol (PEG). Additional water soluble vinyl polymers found useful as glass transition temperature modifiers include poly vinyl alcohol (PVA) and poly vinyl acetate PVAc).

Modified, Water Soluble, Celluloses and Starches

Cellulose and starch derivatives, modified for enhanced water solubility, can also serve as efficient glass transition modifiers. Various modified or derivatized starches can be utilized, including the starch ethers such as hydroxyethyl and hydroxypropyl ether starch. The class of polymers known as cellulose ethers, formed by alkylation of cellulose, are also effective as glass transition modifiers. Cellulose is a linear, unbranched polysaccharide composed of glucopyranose monosaccharide units linked through their 1,4 positions by the $\beta$-anomeric configuration (Kirk-Othmer Encyclopedia, Volume 5, Fourth Edition, ISBN: 0-471-52695-3). The three hydroxyl units per glucopyranose residue can each serve as active sites for ether formation, yielding a maximum degree of substitution (DS) of 3. For water solubility, a DS value of 0.4–2 is generally required. Useful cellulose ethers include hydroxyethyl cellulose (HEC), methyl cellulose, hydroxyethyl methyl cellulose, hydroxypropyl methyl cellulose, and hydroxypropyl cellulose. Commercial examples of HEC include the Cellosize line of products from Dow Chemical Company. Examples of methylcellulose and hydroxypropyl methylcellulose are marketed under the trade name Methocel by Dow Chemical Company.

Processing

Bars of the invention were made by a cast melt process whereby all materials were melted and poured into a mold. The bar materials harden in the mold.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight and all ranges are intended to include not only the ends of the ranges, but all ranges subsumed between the ends as well.

Protocols Used in Invention

Procedure for lather generation from bars:

1. Turn the bar 20 times in water at 90° F. Keep the bar aside for 10 minutes;
2. Turn the bar 10 times in water at 90° F.;
3. Take the bar out of water and shake both hands (plus bar) three times gently to discard excess water. This procedure more or less ensures that a constant quantity of water is used for lather generation.
4. Hold the bar with one hand and rub it on the palm of the other 10 times;
5. Put the bar down, collect all the lather in the center of the palm;
6. Rub this later gently a further 10 times.

Procedure for Determining Specific Gravity Lather Volume:

1. Place a petri dish bottom on a balance and zero the balance;
2. Place a black lid containing a 35×10 mm petri dish lid on the balance and record the weight;
3. Collect the generated later in the bottom of a second petri dish;
4. Weigh the dish plus lather and record the weight as the total weight of lather generated;
5. Carefully remove a small amount of the lather and place it into the lid of the 35×10 mm petri dish;
6. Using the flat edge of a spatula, remove the excess lather by leveling the spatula across the top of the petri dish;

7. Place the lid upside down onto the surface of a black lid from a jar so that the lather touches the jar lid;
8. Reweigh the black lid and the petri dish lid containing the lather;
9. The volume of the 35×10 mm petri dish lid is 5.2 ml;
10. Calculate the weight of lather in the 35×10 mm petri dish lid by subtracting the weight obtained in Step 2 from the weight obtained in Step 8;

COMPARATIVE 1 AND EXAMPLES 1–10

In each of the examples below, bars were prepared by heating and mixing the sugar, the glass transition modifier ($T_g$ modifier), surfactant and water; pouring into a mold and cooling to harden.

Using the process noted above, the following bars were prepared:

| Ingredients | Comparative 1* | Example 1 | Example 2 | Example 3 | Example 4 | Example 5 | Example 6 | Example 7 | Example 8 | Example 9 | Example 10 |
|---|---|---|---|---|---|---|---|---|---|---|---|
| | | | | | Sugar | | | | | | |
| Sucrose | 62.00% | 40.00% | 50.00% | 56.60% | 48.50% | 58.50% | 59.50% | 60.00% | 50.00% | 65.00% | 45.50% |
| | | | | | $T_g$ Modifier | | | | | | |
| Karo Syrup (solid) | | | | | | | | | | 23.00% | |
| Maltodextrin | | 17.60% | | | | | | | | | 22.70% |
| PVP (40K) | | | 16.00% | 5.60% | | | | | | | |
| Polyvinyl Alcohol | | | | | 14.50% | 5.75% | | | | | |
| Polyvinyl Acetate | | | | | | | 5.80% | 2.00% | | | |
| Hydroxypropyl Ethyl Cellulose (Methocel 40-100) | | | | | | | | | 10.00% | | |
| | | | | | Surfactant | | | | | | |
| Na-Laurate | 16.00% | 15.40% | 14.50% | 16.90% | 15.50% | 14.07% | 14.20% | 15.00% | 18.00% | | |
| 60/40 Soap Blend** | | | | | | | | | | | 9.00% |
| Sodium Cocoyl Isethionate (SCI) | | | | | | | | | | 10.00% | |
| Water | 22.00% | 27.00% | 19.50% | 21.69% | 21.50% | 21.68% | 20.50% | 23.00% | 22.00% | 2.00% | 22.80% |

*Because of no $T_g$ modifier, sugar recrystallizes leading to unstable product.
**Refers to 60% tallow soap and 40% coconut soap.

11. The lather specific gravity is calculated by dividing the weight of lather in the 35×10 mm petri dish lid (Step 10) by 5.2 ml (volume of lid). This is a measure of the wetness of the lather. The higher the number, the wetter the lather;
12. The total lather volume is calculated by dividing the total weight of lather generated (Step 4) and dividing by the specific gravity (Step 11);

Procedure for determining wear rate

1. Take initial weight on soap bar;
2. Fill washing bowl with 5 liters of water at desired temperature (40° C.);
3. Wearing waterproof gloves immerse soap bar in water, remove from water and twist 15 times in the hand above water;
4. Repeat step 3;
5. Immerse soap bar in water to wash off lather and place soap bar in a tray;
6. Carry out the full wash procedure (Steps 1–5) six times per day for 4 consecutive days, at evenly spaced intervals during each day (e.g., 9:00, 10:00, 11:00, 12:00, 13:00, 14:00).
7. Calculate rate of wear=(initial weight−final weight).

As seen from the examples, applicants were able to prepare bars in which the sugar was effectively functioning as structurant (because of the presence of glass modifier) and, accordingly, it was possible to prepare bars with low levels of surfactant (mostly soluble fatty acid soaps) and extremely low levels or absence of insoluble fatty acid soaps. From Comparative 1 it can be seen that, where Tg modifier is not used, the sugar recrystallized and product is unstable.

Several points should be noted:

(1) a variety of $T_g$ modifiers can be used;

(2) the surfactant used may be soap, a soap blend or synthetic (e.g., sodium cocoyl isethionate).

EXAMPLES 11–12 and COMPARATIVES 2–3

In order to show that preparation of sugar structured bars did not negatively impact bar properties (as might have been expected), applicants prepared (in the same manner noted for examples above) Examples 11–12 and compared to Comparatives 2 and 3 (which are not sugar structured) as shown below:

| | Example 11 | Example 12 | Comparative 2 (Dove) | Comparative 3 (Lux) |
|---|---|---|---|---|
| Ingredients | | | | |
| Sucrose | 40.00% | 55.00% | | |
| Maltodextrin 250 | 20.00 | | | |
| PVP (40K) | | 5.00% | | |
| Polyvinyl Alcohol | | | | |
| Polyvinyl Acetate | | | | |
| Na-Laurate | 15.00% | 15.00% | | |
| Free Fatty Acid | | | 15–25% | |
| 85/15 | | | 5–15% | 80–90% |
| Sodium Dodecyl Sulfate (SDS) | 2.00% | 2.00% | | |
| SCI | | | 40–50% | |
| Perfume | 1.00% | 1.00% | Minor | Minor |
| Water | 22.00% | 22.00% | 5–10% | 5–10% |
| Properties | | | | |
| Foam (Volume) | 40.35 | 22.48 | 30.00 | 9.00 |
| Gas Fraction | 0.94 | 0.94 | 0.93 | 0.83 |
| Wear rate (g/wash) | 2.04 | 2.24 | 2.30 | 1.70 |

*85% tallow soap an 15% coconut soap.

It can be seen that Example 11 and 12 show that bars can be prepared using blends of synthetic (sodium dodedecyl sulphate) and conventional soap. Further, one can observe the effect of two different modifiers on bar properties.

In the examples, one can also compare the performance of product of the invention relative to two commercial products, Dove® and Lux®.

As can be seen, the sugar structured products of the invention had enhanced lather relative to Lux®. Further, the sugar structured bars had enhanced wear (lower value) relative to Dove®.

In short, it can be seen not only that, quite unexpectedly, it is possible to make the sugar structured bars, but also it can be seen that they can be made without sacrificing user properties.

What is claimed is:

1. Bar composition comprising:

(1) less than about 25% by wt. of surfactant;

(2) greater than about 40% by wt. of sugar or mixture of sugars;

(3) about 5% to 25% by wt. glass transition modifier; and (4) 1% to 30% water.

2. A bar composition according to claim 1 comprising less than about 20% surfactant.

3. A bar composition according to claim 1, wherein the 25% surfactant total surfactant comprise less than 5% insoluble fatty acid soap and/or insoluble synthetic detergent, said percentages being by wt. as a percentage of the total composition.

4. A bar according to claim 3, wherein the 25% surfactant total comprise less than 3% insoluble fatty acid soap and/or insoluble synthetic detergent, said percentages by wt. as a percentage of the total composition.

5. A bar according to claim 4, comprising less than 2% insoluble fatty acid soap and/or insoluble synthetic detergent, said percentages by wt. as a percentage of the total composition.

6. A bar according to claim 1, wherein surfactant comprises greater than about 75% of the total surfactant of soluble fatty acid soap.

7. A bar composition according to claim 1, comprising greater than about 50% sugar, or mixture of sugars.

8. A bar according to claim 1, wherein the glass transition modifier is selected from the group consisting of corn sweeteners, water soluble vinyl polymers and modified, water soluble celluloses and starches.

9. A bar composition according to claim 1, wherein said sugar or sugars comprises sucrose.

* * * * *